United States Patent [19]

Powlan Roy Y.

[11] Patent Number: 4,621,625

[45] Date of Patent: Nov. 11, 1986

[54] LEG TRACTION DEVICE

[76] Inventor: Powlan Roy Y., 1 Chapel Dr., Lafayette, Calif. 94549

[21] Appl. No.: 688,076

[22] Filed: Dec. 31, 1984

Related U.S. Application Data

[63] Continuation-in-part of Ser. No. 543,857, Oct. 20, 1983, abandoned.

[51] Int. Cl.$^4$ ............................................. A61F 5/00
[52] U.S. Cl. ................................................ 128/84 C
[58] Field of Search ...................... 128/80 R, 84 C, 85, 128/94, 80 G, 82, 83

[56] References Cited

U.S. PATENT DOCUMENTS

| | | | |
|---|---|---|---|
| 2,053,753 | 9/1936 | Wellington | 128/84 R |
| 2,601,686 | 7/1952 | Roessler | 128/84 C |
| 2,631,582 | 4/1953 | Bensfield | 128/84 C |
| 2,875,753 | 4/1959 | Sulmonetti | 128/84 R |
| 2,966,905 | 1/1961 | Kamenshine | 128/80 R |
| 3,417,748 | 12/1968 | Bimbler | 128/85 |
| 3,868,951 | 4/1975 | Albrecht | 128/84 C |

Primary Examiner—C. Fred Rosenbaum
Assistant Examiner—Karen L. Kaechele
Attorney, Agent, or Firm—John R. Murtha

[57] ABSTRACT

The disclosure relates to a leg traction system having structure for supporting the leg and applying axial force to the leg. A rigid vector bar is positioned above the knee and lower leg, a pulley system including a cable and weight is connected at one end to the leg supporting structure and at the other end to the vector bar.

15 Claims, 7 Drawing Figures

LEG TRACTION DEVICE

This is a continuation-in-part application of my copending application Ser. No. 543,857, filed Oct. 20, 1983, now abandoned.

The invention relates to leg traction systems and, more particularly, to an improved traction system for use in treating fractures of the femur.

When a fracture of the femur bone occurs a shortening of the patient's thigh results due to tonic contraction of the long muscles that connect the pelvis and the tibia and fibula. There are two sets of opposing muscles, the hamstrings and the rectus femoris, which are normally slightly stretched by the femur bone. But when the femur is broken the muscles are allowed to contract and this results in displacement and overriding of the fragmented bone ends and a consequent shortening of the patient's thigh. Before the fracture can be healed the fragmented bone ends must be repositioned and maintained in their normal relationship. Principal therapy in the case of a fractured femur, accordingly, has included traction to accomplish this repositioning and maintenance of the bone fragments.

One widely used form of management for fracture of the femur consists of the application of Buck's traction. This form of traction comprises the application of a longitudinal traction force to a traction boot attached to the patient's lower leg while the leg is stretched out straight on the bed. Application of this form of traction is uncomfortable because the knee of the patient is out straight and a pull through a completely extended knee is uncomfortable. Sometimes a pillow is placed beneath the knee to flex it and make it more comfortable. Rotation of the leg in this form of traction cannot be controlled, however, and the muscles attached to the upper fragment tend to make the hip lie in a slightly flexed position. Accordingly, when the leg is pulled out straight there is a tendency to angulation at the fracture site with consequent pain and muscle spasm. Additionally, the lack of alignment of the broken bones does not permit healing with this condition.

Another widely used form of management employs what is known as Russell's traction. In this system of traction an upwardly angled force is applied behind the knee to bring it into a much more comfortable flexed position. This upward force also flexes the hip slightly. The rope holding the sling behind the knee passes over a pair of pulleys located opposite the patient's lower leg and is connected thereto through a suitable traction boot. This arrangement thus applies an additional force along the axis of the flexed lower leg portion of the patient. The advantage of this system is that the resultant of the applied forces is along the axis of the upper leg where the fracture has occurred. The main disadvantage is that the pulley setup is quite critical if the resultant force, or direction of pull, is to be along the line of the axis of the upper leg. The use of dual pulleys requires their careful positioning so that the rope lines at these pulleys are parallel to each other. If they are not parallel, the active force on the lower leg is less and this causes the line of the resultant force to vary from the desired path. This, in turn, may result in misalignment of the fractured femur. Another disadvantage of this system is that it requires the setup of a pulley system at the foot of the bed, something which is difficult to accomplish as a practical matter if the bed has a solid footboard. Moreover, the attachment to the patient's lower leg prevents all but slight movement of the leg and interferes with the patient's ability to exercise the knee joint. This often leads to stiffness of the joint and much discomfort to the patient. Still another disadvantage of this system is that as the direction of pull on the lower leg is fixed and cannot be changed, a shift in the patient's body position may result in angulation of the fracture site. For this reason the use of Russell's traction requires the patient to remain essentially in the same position with little movement and this is a definite disadvantage to its use.

Another form of management of a fracture of the femur is called Balanced Traction. Since it is very difficult and timeconsuming to set up, it is usually reserved for those cases in which the fracture will be definitively treated with traction for the entire healing term. This form of traction requires the use of three different weights and the insertion of Steinmann pins in the femur and the tibia. The complexity and difficulty of setting up this system of traction limits its usefulness.

The object of the present invention is to provide improved traction for treating fractures of the femur and other fractures of the leg which is easily set up, simple in application and does not restrict the patient's freedom of movement.

A preferred embodiment of the invention is shown in the accompanying drawings in which.

Figure 1:
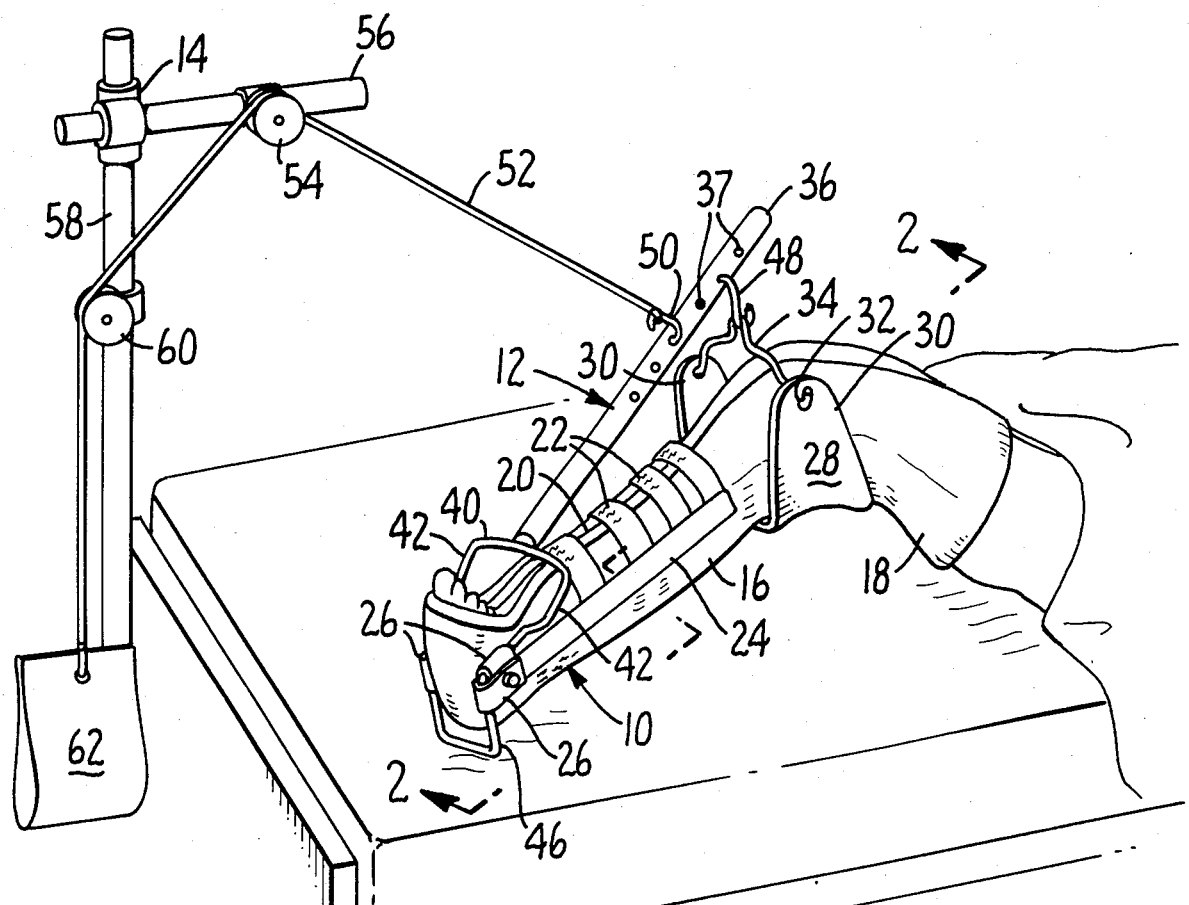
FIG. 1 is a perspective view showing the application of the applicant's traction to a patient in bed.
Figure 3:
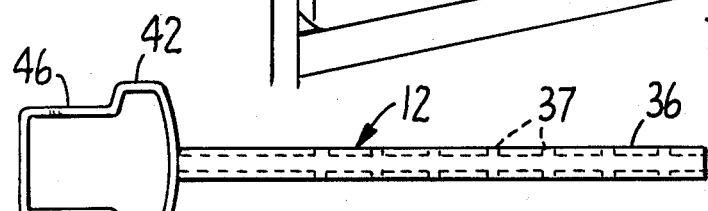
FIG. 3 is a top elevational view of the vector bar which serves to apply the component forces suspending the knee and applying traction to the leg.
Figure 4:
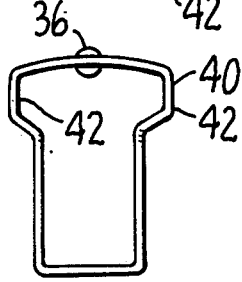
FIG. 4 is an end elevational view of the foot stand for the vector bar.
Figure 2:
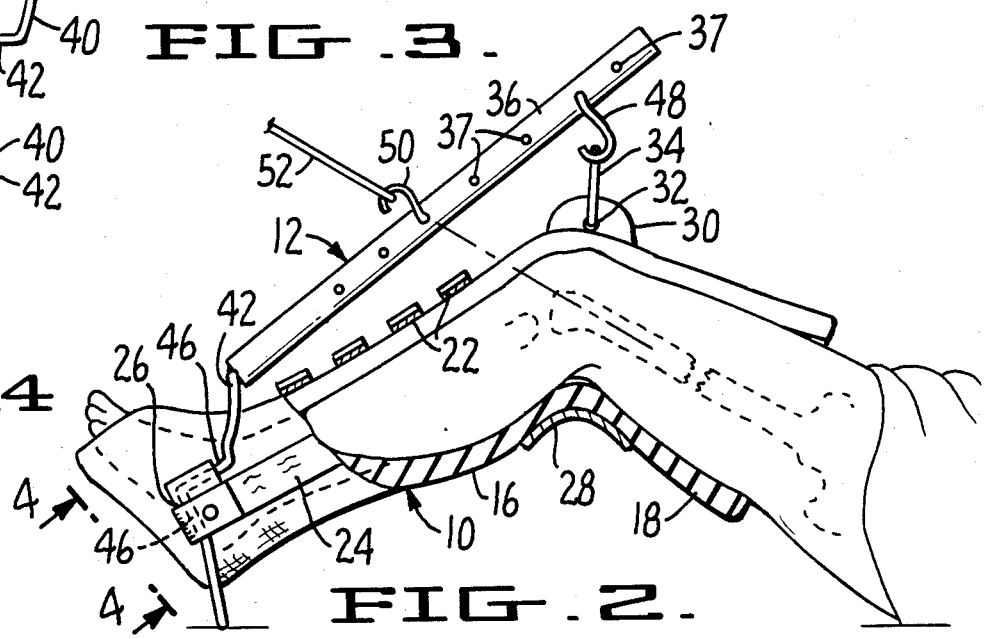
FIG. 2 is a sectional view taken along the line 2—2 in FIG. 1.

As seen in FIGS. 1 and 2, the preferred embodiment of the invention comprises an improved traction boot 10 and a unique vector bar 12 in conjunction with a standard pulley support system 14. In the past it has been customary to apply a traction boot to the lower extremity of the patient's leg. In the novel and improved form shown in the drawings, the boot 10, not only has the customary lower portion 16 that is applied to the lower extremity of the patient's leg, but also an upper portion 18 that is applied to the patient's thigh above the knee. As usual, the boot casing is made from plastic foam and is shaped to generally conform to the contours of the patient's leg. A split 20 runs along the length of the boot 10 at its top to permit application of the boot to the patient. A plurality of transverse, velcro-type straps 22,22 are provided on the lower portion 16 of the boot for fastening the boot to the patient's leg. A pair of longitudinal straps 24,24 are also provided with each strap secured to the boot 10 on opposite sides of the leg. The straps 24,24 are each formed with a pair of loops 26,26 at their ends by means of which the straps, and hence the boot, may be connected to the vector bar so as to exert a longitudinal force on the lower extremity of the patient's leg as will be described in more detail hereinafter. It will be realized that the longitudinal pull on the patient's lower leg is applied to the leg only through the skin friction generated by the traction boot. As long as the amount of force applied is not too great no problems arise, but if the force is increased, a point is reached when the boot starts to pull off the patient's leg. By adding an extra thigh portion 18 to the traction boot, applicant increases the amount of skin friction between the boot and the patient's leg and gains the additional resistance to slippage that occurs by reason of the boot's being positioned above the saddle 28 behind the knee.

Positioned behind, or underneath, the patient's knee is a suspension saddle 28 whereby a lifting force may be applied to the knee to suspend it in a flexed position substantially as shown in the drawings. In the form shown, the saddle 28 comprises a U-shaped plastic member having side arms 30,30 with holes 32,32 at their upper ends to receive a suspension yoke 34. The particular means for suspending the knee is not critical except that the suspension must be such as to allow movement of the knee without cutting off circulation of blood in the patient's leg. A cloth sling could be used as long as some means were provided to prevent the sling from bunching up and closing off circulation in the leg.

As in the case of Russells traction, the applicant's traction system both lifts the patient's leg at the knee and pulls on the lower leg. The resultant of these force components lies along the axis of the upper leg where the fracture has occurred. This result, however, is accomplished in a much simpler way through the use of the vector bar 12. The vector bar 12 comprises a rigid, one-piece member that is about as long as the patient's lower leg and is positioned immediately above it. At its upper end, that is, the end nearest the patient's torso, the bar 12 comprises a longitudinal section 36 having a series of evenly spaced holes 37,37 formed therein, This longitudinal section 36 of the arm 12 is joined to a rod-like stand, or support, 40 that straddles the patient's foot and the traction boot 10. The stand 40 includes a pair of arms 42,42 disposed parallel to each other and connected by a bar 44. Approximately mid-way of their length, the arms 42,42 are formed with two straight sections 46,46 positioned at right angles to one another. It is these sections 46,46 that receive the loops 26,26 on the straps 24,24 whereby the traction boot 10 is connected to the vector bar 12. Immediately above these sections the arms 42,42 flare outwardly so as to provide a wider opening around the patient's foot in the traction boot and then curve back to join the longitudinal section 36. It is important to note that the stand 40 supports the vector bar 12 independently of the patient's leg and the traction boot 10. When the traction device is in its operative position, the suspension yoke 34 for the saddle 28 is held by a hook 48 selectively positioned in one of the holes 37,37 in the upper section of the vector bar.

A second hook 50 is selectively secured to the vector bar 12 at a point intermediate the suspension hook 48 and the support 40 for the bar. The hook 50 serves to connect the vector bar 12 with a supporting cable 52. The cable 52 is passed over a pulley 54 mounted on an arm 56 of a standing support 14 The cable 52 passes over a second pulley 60 that is mounted on the vertical column 58 of the stand 14 and terminates in a weight carrier 62. The carrier 62 holds the amount of weight required to assert the desired amount of pull on the patient's leg.

The selection of the hook 50 in the holes 37,37 of the vector bar 13 and the angle of the cable 52 are chosen so that the resultant force of the traction device on the patient will be along the axis of the patient's upper leg and the amount of force applied will be such as to assert the desired amount of pull. The selection of the location of the location of the hook 50 also determines the angle at which the patient's leg and knee will be flexed.

It will be noted that applicant's traction system retains the chief advantage of Russell's traction—a resultant pulling force along the axis of the upper leg—with a markedly simpler arrangement of components. The two pulleys normally disposed at the foot of the bed in Russell's traction have been eliminated along with their consequent problems. Another important feature of the applicant's system is that the patient's foot and lower leg have been freed from the constriction imposed by the connection to the two pulleys at the foot of the bed. In applicant's traction the patient's leg is free floating from the single suspension point on the vector bar 12. This permits the patient to move his or her lower leg or body to nearly any position desired and to roll from side to side. This greater freedom of movement results in decreased bed sores and facilitates nursing of the patient. The vector bar 12 still applies proper traction force and proper vector angle in three planes; side to side, up and down and axially.

Figure 5:
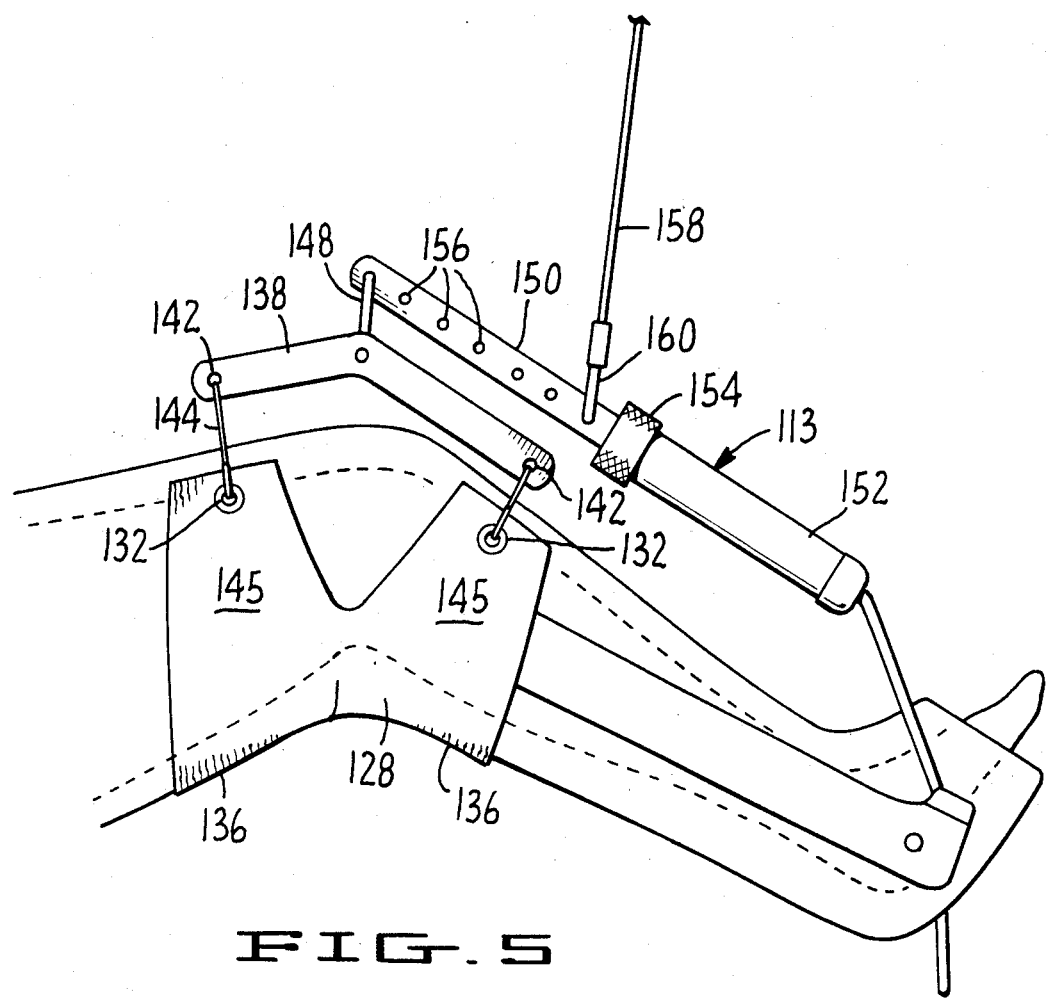
FIG. 5 is a side elevational view of modified form of the invention with an improved method of supporting the patient's leg.
Figures 6, 7:
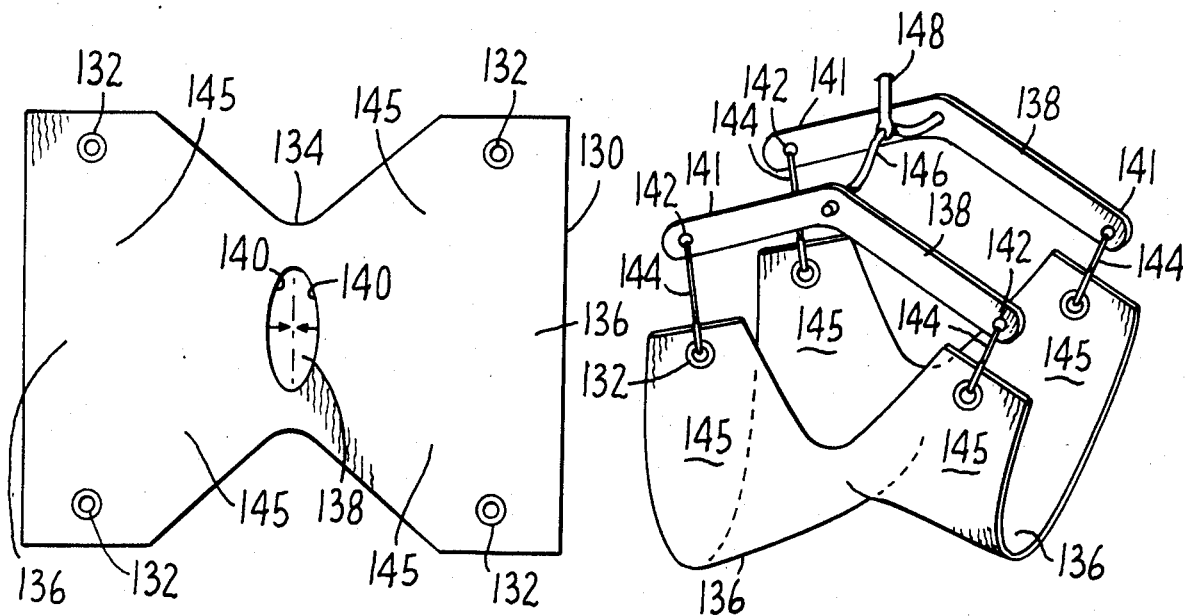
FIG. 6 is a perspective view of the apparatus shown in FIG. 5 for supporting the patient's leg.
FIG. 7 is a plan view showing the fabric panel for the improved sling for supporting the patient's leg.

In the modified form of the invention shown in FIGS. 5-7 significant changes have been made in the vector bar and in the means for supporting the patient's leg. The plastic saddle 28 has been replaced by an improved sling arrangement for supporting the patient's leg in a comfortable, flexed position. A canvas or cloth sling 128 is positioned underneath the traction boot 116 adjacent the patient's knee. As is best seen in FIG. 7, the sling 128 is made from a substantially rectangular fabric panel 130. The panel is provided with two pairs of oppositely disposed fastening means 132,132. In the preferred form of the invention shown here, the fastening means comprise two pairs of grommets located adjacent the four corners of the panel. Two substantially triangular cut-outs 134,134 are made in the panel intermediate the ends 136,136. A football-shaped, eliptical cut-out 138 is also made midway between the ends of the panel 130 and the edges 140,140 of this cut-out are then sewn together. This modification of the panel has the effect of shortening it along a central axis and disposing the opposite end portions 136,136 of the panel in approximately the same inclination as the patient's lower thigh and upper calf when the knee is slightly flexed.

Suspension of the sling 128 is accomplished by means of a pair of substantially parallel suspension arms 138,138. Each of the arms 138,138 is slightly bent so as to roughly conform to the curvature of the patient's leg at the knee and the arms are long enough to dispose the ends 141,141 thereof above and below the patient's knee joint. At each end of the arms 141,141 an opening 142,142 is provided for a hook 144,144 that connects the opening 142,142 in the arm with the adjacent grommet 132,132 in the sling. This arrangement causes the sides 145,145 and the ends 136,136 of the sling to fit around the patient's leg and form a cradle that supports the leg comfortably in a slightly flexed position. A central yoke 146 interconnects the suspension arms 138,138 adjacent their midpoints and the yoke carries a primary suspension hook 148 that suspends the sling and the suspension arms from the vector bar 113 of the traction device.

This sling and suspension arrangement provides a means of supporting the patient's leg in a comfortable, flexed position without any tendency on the part of the sling to ride up or bunch up behind the patient's knee.

The reason for this is that the supporting forces on the sling are applied at points above and below the patient's knee joint and are directed by the suspension arms outwardly away from the patient's knee. The fashioning of the sling panel in the same approximate inclination as the patient's leg also aids in eliminating any tendency of the sling to bunch up behind the knee.

The vector bar 113 is of a two-piece construction having an upper portion 150 that telescopically slides in and out of a slightly larger lower portion 152. A knurled nut 154 can be tightened to control the spacing of the upper portion 150 within the lower portion 152. This feature permits the vector bar to be selectively lengthened or shortened to correspond to the length of the patient's leg thereby enabling one vector bar to accommodate all patients regardless of the variation in the length of their legs.

The upper portion 150 of the vector bar is provided with a series of spaced holes 156,156 which serve at connection points for the supporting cable 158 and hook 160. By varying the point of connection among these spaced holes 156,156 and by varying the angle of the supporting cable 158, the amount of resultant force exerted along the axis of the patient's upper leg may be varied as desired.

I claim:

1. A traction system for use in treating leg fractures in a human patient, said system comprising:
   (a) first means adapted to support the patient's knee and to maintain the leg in a flexed position,
   (b) second means adapted to support the patient's lower leg, said second means being secured thereto so as to transmit an axial force from said second means to the patient's lower leg,
   (c) a rigid, vector bar positioned immediately above and longitudinally along the patient's knee and lower leg and connected to said first and second means at two separately spaced points, and
   (d) a pulley system including at least one pulley selectively fixed on a support and having a cable passing over said pulley, said cable being connected to a selected weight at one end and, at the other end, being connected to the vector bar intermediate said connection points with said first and second means whereby a steady and stable upward force is applied to the patient's knee by said first means and a steady and stable force is applied along the axis of the patient's lower leg by said second means.

2. A traction system as set forth in claim 1 wherein the length of said vector bar is selectively adjustable.

3. A traction system as set forth in claim 1 wherein said vector bar is provided with a plurality of connection points whereby said cable from the pulley may be selectively connected to the vector bar.

4. A traction system as set forth in claim 3 wherein said vector bar is provided with a plurality of connection points for said first means whereby the connection point on the vector bar for said first means may be selectively varied.

5. A traction system as set forth in claim 4 wherein said first means comprise a sling under the patient's knee that is connected to the vector bar.

6. A traction system for application to the leg of a human patient, said system comprising:
   (a) a sling adapted to pass under the patient's knee,
   (b) a traction boot having means for affixing the boot to the lower leg of the patient and longitudinal straps extending beyond the patient's foot,
   (c) a rigid vector bar positioned above the patient's knee and lower leg, said bar having a hook to engage said sling and a plurality of holes to seltively vary the position of said hook, said bar having a rigid support depending from the lower end of the bar to engage the longitudinal straps on the traction boot, and
   (d) a pulley system having at least one pulley mounted on a fixed support and having a cable passing over said pulley, said cable being connected to a second hook positioned on the vector bar, said bar having a plurality of holes to selectively vary the position of said second hook, the position of said second hook always being intermediate the position of the hook for the sling and the rigid support at the lower end of the vector bar.

7. A traction system for use in treating leg fractures in a human patient, said system comprising:
   (a) first means for supporting the patient's knee in a flexed position, said means comprising a sling under the patient's knee,
   (b) second means adapted to apply an axial force to the patient's lower leg,
   (c) a rigid vector bar positioned above the patient's knee and lower leg, said bar being connected to said first means and said second means, and
   (d) a pulley system including at least one pulley mounted on a fixed support and having a cable passing over said pulley, said cable being connected to a selected weight at one end and at the other end to the vector bar intermediate said connection points on the bar to the first and second means,
   (e) said vector bar having a selectively adjustable length and being provided with a plurality of connection points for both the cable and said first means whereby the connection point on the vector bar for said cable and first means may be selectively varied,
   (f) said sling comprising a fabric panel having two pairs of fastening means disposed adjacent the corners of the panel and the vector bar is provided with means over the patient's leg for suspending the panel by said fastening means, one pair of said means being suspended from a point on the suspending means positioned below the patient's knee and the other of said fastening means being suspended from a point on the suspending means positioned above the patient's knee.

8. A traction system as set forth in claim 7 wherein said second means comprise a traction boot with longitudinal straps that are engaged by a rigid connection positioned at the end of the vector bar.

9. A traction system as set forth in claim 8 wherein said traction boot is provided with a thigh portion for engagement with the patient's leg above the knee.

10. A traction system as set forth in claim 7 wherein said sling comprises a fabric panel having two pairs of fastening means disposed adjacent the corners of the panel and the vector bar is provided with means over the patient's leg for suspending the panel by said fastening means, one pair of said fastening means being suspended from a point on the suspending means positioned below the patient's knee and the other pair of said fastening means being suspended from a point on the suspending means positioned above the patient's knee.

11. A traction system as set forth in claim 10 wherein said fabric panel is foreshortened along a central axis.

12. A traction system as set forth in claim 10 wherein said fabric panel is foreshortened along a central axis.

13. A traction system as set forth in claim 12 wherein said fabric panel is foreshortened midway between the ends of the panel.

14. A traction system as set forth in claim 10 wherein said suspension means comprise a pair of substantially parallel arms positioned over the patient's leg at the knee that extend above and below the patient's knee.

15. A traction system as set forth in claim 14 wherein said parallel arms are disposed substantially over the opposite sides of the patient's leg and are supported by the vector bar at a point between them.

* * * * *